(12) United States Patent
Zanidaki et al.

(10) Patent No.: US 12,343,890 B2
(45) Date of Patent: Jul. 1, 2025

(54) SOLID SHAVING AID COMPOSITION

(71) Applicant: Bic Violex Single Member S.A., Attiki (GR)

(72) Inventors: Maria-Thiresia Zanidaki, Attiki (GR); Georgios Vlachos, Attiki (GR)

(73) Assignee: BIC Violex Single Member S.A., Anoixi (GR)

( * ) Notice: Subject to any disclaimer, the term of this patent is extended or adjusted under 35 U.S.C. 154(b) by 601 days.

(21) Appl. No.: 17/804,612

(22) Filed: May 31, 2022

(65) Prior Publication Data
US 2022/0388189 A1   Dec. 8, 2022

(30) Foreign Application Priority Data
May 31, 2021   (EP) .................................... 21176921

(51) Int. Cl.
*B26B 21/44*   (2006.01)
*A45D 40/26*   (2006.01)
(Continued)

(52) U.S. Cl.
CPC ............ *B26B 21/443* (2013.01); *A45D 40/26* (2013.01); *A61G 9/02* (2013.01); *A61K 8/0216* (2013.01);
(Continued)

(58) Field of Classification Search
CPC .... B26B 21/443; A45D 40/26; A61K 8/0216; A61K 8/345; A61K 8/375; A61K 8/891; A61Q 9/02
See application file for complete search history.

(56) References Cited

U.S. PATENT DOCUMENTS 7,811,553 B2 *  10/2010  O'Grady ................. B26B 21/44
                                                30/32
8,524,207 B2     9/2013  Ellis et al.
(Continued)

FOREIGN PATENT DOCUMENTS

EP   1704897 A1   9/2006
EP   1868778 B1   3/2010
(Continued)

OTHER PUBLICATIONS

Extended European Search Report issued in European Patent Application No. 21176921.1, dated Dec. 14, 2021.

*Primary Examiner* — Omar Flores Sanchez
(74) *Attorney, Agent, or Firm* — Bookoff McAndrews, PLLC

(57) ABSTRACT

The present disclosure describes a razor cartridge including a housing having a front edge and a rear edge; shaving blades disposed between the front edge and the rear edge; and at least one shaving bar disposed in front of the blade(s) and/or rear of the blade(s) which includes a solid shaving aid composition that includes, relative to the total weight of the solid shaving aid composition: about 15 wt.-% to about 48 wt.-% of a soap base including of one or more fatty acid salts having from about 8 to about 24 carbon atoms and optionally one or more fatty acids having from about 8 to about 24 carbon atoms, at least about 35 wt.-% of one or more polyols including from ~2 to ~8 carbon atoms; the polyol selected from a group including glycerol, sorbitol, ethylene glycol, diethylene glycol, propylene glycol, dipropylene glycol, tripropylene glycol, methylpropane diol glycol.

20 Claims, 1 Drawing Sheet

(51) Int. Cl.
    *A61G 9/02*          (2006.01)
    *A61K 8/02*          (2006.01)
    *A61K 8/34*          (2006.01)
    *A61K 8/37*          (2006.01)
    *A61K 8/891*         (2006.01)

(52) U.S. Cl.
    CPC .............. *A61K 8/345* (2013.01); *A61K 8/375* (2013.01); *A61K 8/891* (2013.01)

(56) References Cited

U.S. PATENT DOCUMENTS

| | | | |
|---|---|---|---|
| 8,557,229 B2 | 10/2013 | Smith et al. | |
| 9,119,796 B2 | 9/2015 | Cook et al. | |
| 10,342,754 B2 * | 7/2019 | Bousvaros | A61K 8/678 |
| 2007/0110703 A1 | 5/2007 | O'Grady et al. | |
| 2007/0241306 A1 * | 10/2007 | Wehner | C11C 3/003 |
| | | | 252/364 |
| 2007/0269392 A1 * | 11/2007 | Sunkara | A61P 43/00 |
| | | | 424/59 |
| 2011/0178181 A1 * | 7/2011 | Bakes | A61Q 9/02 |
| | | | 514/691 |
| 2012/0094006 A1 | 4/2012 | Kwiecien | |
| 2012/0216408 A1 * | 8/2012 | Cook | A61Q 9/02 |
| | | | 30/41 |
| 2014/0245613 A1 | 9/2014 | Good et al. | |
| 2014/0366381 A1 | 12/2014 | Phipps et al. | |
| 2015/0273711 A1 | 10/2015 | Wang et al. | |
| 2016/0338928 A1 | 11/2016 | Haught et al. | |
| 2017/0002289 A1 * | 1/2017 | Stephens | A61K 8/342 |
| 2017/0239466 A1 * | 8/2017 | Cazares Delgadillo | A61K 8/11 |
| 2018/0008843 A1 | 1/2018 | Zannoni et al. | |
| 2022/0388189 A1 * | 12/2022 | Zanidaki | A61K 8/895 |
| 2024/0110118 A1 * | 4/2024 | Lee | B26B 21/443 |
| 2024/0238999 A1 * | 7/2024 | Zanidaki | A61K 8/0216 |

FOREIGN PATENT DOCUMENTS

| | | |
|---|---|---|
| EP | 2627303 B1 | 8/2016 |
| EP | 2900332 B1 | 8/2017 |
| EP | 2964432 B1 | 8/2018 |
| EP | 2591895 B1 | 2/2019 |
| EP | 3478246 B1 | 10/2020 |
| WO | 2016/162080 A1 | 10/2016 |
| WO | 2018/009743 A1 | 1/2018 |
| WO | 2018/009744 A1 | 1/2018 |

* cited by examiner

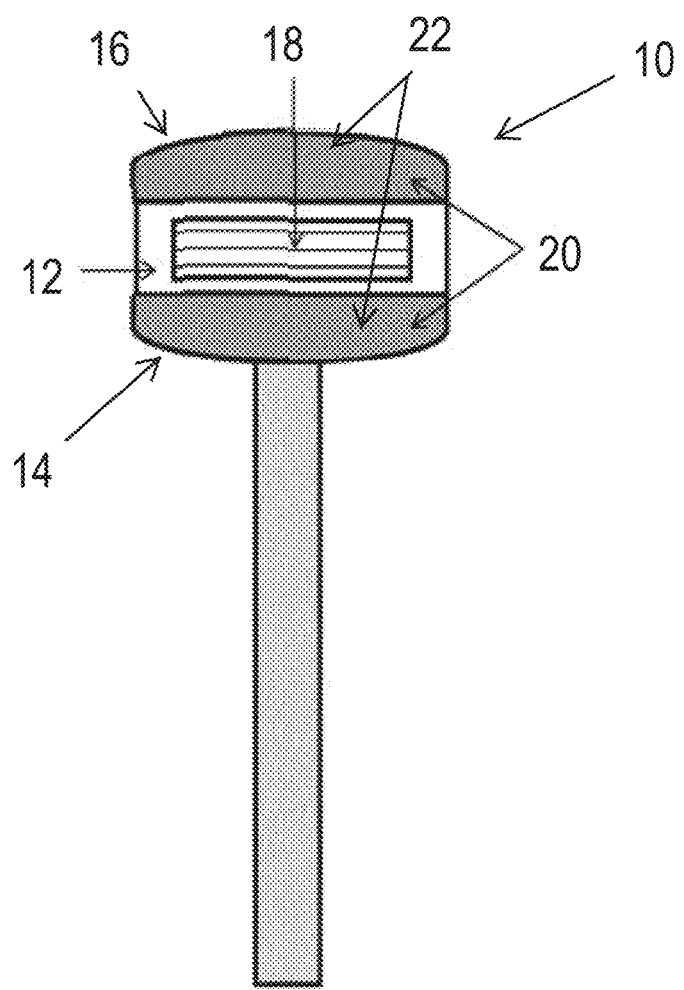

SOLID SHAVING AID COMPOSITION

CROSS REFERENCE TO RELATED APPLICATION

This application claims priority from European Application No. EP21176921.1, filed on May 31, 2021, the entire contents of which being incorporated herein by reference.

TECHNICAL FIELD

The present disclosure relates to the field of razor cartridges. More specifically, the present disclosure relates to razor cartridges comprising solid shaving aid compositions.

BACKGROUND

Razors generally include a handle and a razor cartridge fixedly or releasably attached to the handle. The razor cartridge includes at least one blade for shaving hair. The razor cartridge may also include a solid shaving aid composition, often in the shape of a shaving aid bar extending parallel to at least one blade. The user holds the handle and repeatedly moves the razor across an area of the body to be shaved, e.g., the face, until hair is removed from the surface of the body. The shaving aid bar may function to aid in shaving and to decrease or prevent skin irritation due to the repeated exposure of the skin to sharp razor blades.

Razor cartridges comprising such solid shaving aid compositions are known in the art, for instance from WO 2016/162080 A1. However, while successful in aiding with comfortable and simplified shaving, there is still room for improvement. For instance, current products may still benefit from a closer shave, i.e. the ability to smoothly shave so close to the skin with a minimum number of strokes to provide the user with a feeling of a stubble-free skin.

SUMMARY

Following diligent research, a new formulation principle was identified which provides an improved close shave while maintaining good durability, i.e. long acceptance by the user.

According to a first aspect, the present disclosure relates to a razor cartridge comprising a housing having a front edge and a rear edge. The housing comprises one or more shaving blades disposed between the front edge and the rear edge. At least one shaving bar is disposed in front of the blade(s) and/or rear of the blade(s). The shaving bar comprises a solid shaving aid composition. The solid shaving aid composition may comprise, relative to the total weight of the solid shaving aid composition:
about 15 wt.-% to about 48 wt.-% of a soap base consisting of one or more fatty acid salts having from about 8 to about 24 carbon atoms and optionally one or more fatty acids having from about 8 to about 24 carbon atoms;
at least about 35 wt.-% of one or more polyols comprising from about 2 to about 8 carbon atoms, wherein the polyol is in particular selected from the group consisting of glycerol, sorbitol, ethylene glycol, diethylene glycol, propylene glycol, dipropylene glycol, tripropylene glycol, methylpropane diol glycol, and mixtures thereof; and
about 0.1 to about 3 wt.-% of one or more silicone cross-polymers.

In some embodiments, the one or more polyols may include polyols comprising from about 2 to about 8 carbon atoms and from about 2 and about 7, more specifically from about 2 and about 6, hydroxyl groups; or a mixture of several such compounds.

In some embodiments, the one or more polyols may comprise a mixture of glycerol and sorbitol or a mixture of glycerol, sorbitol and one or more further polyols selected from the group consisting of propylene glycol, ethylene glycol, diethylene glycol, dipropylene glycol, tripropylene glycol, and methylpropane diol glycol.

In some embodiments, at least about 15 wt.-%, in particular at least about 20 wt.-%, of the one or more polyols may have a melting point below about 34° C.

In some embodiments, the solid shaving aid composition my comprises, as one or more polyols, relative to the total weight of the solid shaving aid composition: about 15 to about 45 wt.-%, in particular about 17 to about 40 wt.-%, glycerol; about 5 to about 25 wt.-%, in particular about 6.5 to about 22 wt.-%, sorbitol; and about 1.5 to about 9.5 wt.-%, in particular about 2.5 to about 8.5 wt.-%, of a compound selected from propylene glycol, ethylene glycol, dipropylene glycol, tripropylene glycol, methylpropane diol glycol, and mixtures thereof, in particular propylene glycol.

In some embodiments, the one or more silicone cross-polymers may comprise an emulsifying silicone cross-polymer.

In some embodiments, the one or more silicone cross-polymers may comprise a first (di)methicone-based polymer chain which is crosslinked to a second (di)methicone-based polymer chain via at least one hydrophilic oligomer/polymer chain.

In some embodiments, the first and/or second dimethicone-based polymer chain may be selected from dimethicone and optionally substituted linear or branched saturated or unsaturated $C_1$-$C_{20}$ alkyl (di)methicone.

In some embodiments, the hydrophilic oligomer/polymer chain may be a $C_1$-$C_4$-alkyl polyether wherein the $C_1$-$C_3$-alkyl residues are optionally substituted with hydroxyl, hydroxyl-$C_1$-$C_4$-alkyl, $C_1$-$C_4$-alkyl ether groups or hydroxyl-$C_1$-$C_4$-alkylether groups, in particular polyethylene glycol, polypropylene glycol, polyglycerol, and polysorbate.

In some embodiments, the one or more silicone cross-polymer may comprise polyglycerine-modified cross-linked polymers, polyether-modified cross-linked polymers, polyether/alkyl co-modified cross-linked polymers, polyglycerine/alkyl co-modified cross-linked polymers, dimethicone/vinyl dimethicone cross-polymers, dimethicone/phenyl vinyl dimethicone cross-polymers, vinyl dimethicone/lauryl dimethicone cross-polymers, dimethicone crosspolymers, $C_{30-45}$-alkyl cetearyl dimethicone cross-polymers, cetearyl dimethicone cross-polymers, in particular dimethicone/vinyl dimethicone cross-polymers, vinyl dimethicone/lauryl dimethicone cross-polymers, vinyl dimethicone/lauryl dimethicone cross-polymers, lauryl dimethicone/polyglycerin cross-polymers, dimethicone/polyglycerin cross-polymers, polyethylene glycol/polypropylene glycol-dimethicone cross-polymer; and mixtures thereof.

In some embodiments, the one or more silicone cross-polymers may be present in amounts of about 0.1 to about 1.0 wt.-%, more specifically between about 0.15 to about 0.7 wt.-%, and in particular between about 0.20 wt.-% and about 0.45 wt.-%, relative to the total weight of the solid shaving aid composition.

In some embodiments, the solid shaving aid composition may further comprise one or more oils, in particular one or more oils comprising a glycerol esterified with three fatty acids.

In some embodiments, the one or more oils may comprise one or more humectant oils having a molecular weight of greater than about 500 g/mol, more specifically a castor oil derivative, even more specifically a castor oil ester and in particular castoryl maleate.

In a further aspect, the present disclosure relates to a solid shaving aid composition having a composition as defined for the first aspect of the present disclosure.

In some embodiments, the solid shaving composition may be shaped into the form of a bar, more specifically a bar configured to be placed onto a razor cartridge, and in particular a bar having a length of between about 30 mm to about 80 mm, a width between about 2 mm and about 10 mm, and a depth of about 0.2 mm to about 4 mm.

BRIEF DESCRIPTION OF THE DRAWINGS

FIG. 1 shows a razor cartridge including a housing including at least one shaving bar including a solid shaving aid composition, according to aspects of the disclosure.

DETAILED DESCRIPTION

Hereinafter, a detailed description will be given of the present disclosure. The terms or words used in the description and the claims of the present disclosure are not to be construed limitedly as only having common-language or dictionary meanings and should, unless specifically defined otherwise in the following description, be interpreted as having their ordinary technical meaning as established in the relevant technical field. The detailed description will refer to specific embodiments to better illustrate the present disclosure, however, it should be understood that the presented disclosure is not limited to these specific embodiments.

In a first aspect, and with respect to FIG. 1, the present disclosure relates to a razor cartridge 10 comprising a housing 12 having a front edge 14 and a rear edge 16. The housing 12 comprises one or more shaving blades 18 disposed between the front edge 14 and the rear edge 16. At least one shaving bar 20 is disposed in front of the blade(s) 18 and/or rear of the blade(s) 18.

The shaving bar 20 comprises a solid shaving aid composition 22. The solid shaving aid composition may comprise, relative to the total weight of the solid shaving aid composition: about 15 wt.-% to about 48 wt.-% of a soap base consisting of one or more fatty acid salts having from about 8 to about 24 carbon atoms and optionally one or more fatty acids having from about 8 to about 24 carbon atoms; at least about 35 wt.-% of one or more polyols comprising from about 2 to about 8 carbon atoms, wherein the polyol is in particular selected from the group consisting of glycerol, sorbitol, ethylene glycol, diethylene glycol, propylene glycol, dipropylene glycol, tripropylene glycol, methylpropane diol glycol, and mixtures thereof; and about 0.1 to about 3 wt.-% of one or more silicone cross-polymers. Unless expressly stated otherwise, all references in this disclosure to wt.-% refer to the wt.-% in relation to the total weight of the solid shaving aid composition.

As indicated above, the present disclosure provides a new formulation which is endowed with improved close shave while maintaining good durability. These findings are confirmed by panel tests of exemplary compositions according to the present disclosure and will be further elaborated in the experimental section.

Without wishing to be bound by theory, it is believed that the combination of a relatively high amount of moisturizing polyols in a fatty acid salt-based soap composition with a silicone cross-polymer is providing the aforementioned benefit: The high amount of moisturizing agents are able to penetrate into the skin and hair and set it up for the blade's cutting action without nicking so as to facilitate a closer shave. However, the relatively high amount of water-soluble polyols may also result in excessive and premature dissolution of the solid shaving of the shaving aid. The provision of the silicone cross-polymer may counter said excessive dissolution while not being overly detrimental to the overall performance of the shaving aid: Again without wishing to be bound by theory, it is believed that the thickening property of the silicone cross-polymer contributes to the formation of a thicker emulsion on the surface of the solid shaving aid which may help in preventing excessive solubilization and premature loss of the solid shaving aid. Thus, it contributes to the durability of the shaving aid. At the same time, the thixotropic properties of the silicone cross-polymers contribute to a smooth gliding action of the blades close to the skin and hairs during the shaving action.

The shaving bar 20 is not particularly limited and can have any suitable shape. Typically, it is in the form of at least one strip or another elongated body which is arranged substantially parallel to the shaving blades. The shaving bar 20 comprises the shaving aid composition 22. The shaving aid composition 22 is solid for the present purposes, i.e. solid in the sense that the shaving aid composition retains its shape once applied to the cartridge and does not migrate or "run off" under normal storage conditions (e.g. temperature of up to about 25° C. and a relative humidity of up to about 60%) and/or intended use conditions. However, it should be understood that the solid state of the shaving aid composition is not particularly limited and also includes wax-like characteristics. The shaving aid composition may be solid at room temperature, e.g. at about 25° C.

The solid shaving aid composition 22 may comprise about 15 wt.-% to about 48 wt.-% a soap base consisting of one or more fatty acid salts having from about 8 to about 24 carbon atoms and optionally one or more fatty acids having from about 8 to about 24 carbon atoms. The term fatty acid is well-established in this technical filed and is in particular meant to include a monovalent linear carboxylic acid having between about 8 and about 24 carbon atoms. When referring to the soap base in the present disclosure, it should be understood that this is referring to the sum of the aforementioned fatty acid salts and fatty acids as a (major) component of the soap solid shaving aid. Additionally or alternatively, the soap base may be defined as the total summed-up amount of the aforementioned fatty acid salts and, if present, fatty acids.

In some embodiments, the one or more fatty acid salts may comprise one or more monovalent linear or branched saturated or unsaturated carboxylic acid salts having between about 8 and about 24 carbon atoms, in particular between about 10 and about 20 carbon atoms. In some embodiments, the solid shaving aid composition may optionally comprise one or more monovalent linear or branched saturated or unsaturated carboxylic acids having between about 8 and about 24 carbon atoms, in particular between about 10 and about 20 carbon atoms. The fatty acid salts may be partly substituted by said fatty acids, e.g. from about 0.1 to about 20 wt.-%, in particular from about 1 to about 10 wt.-%, relative to the total weight of the fatty acid salts.

In some embodiments, the one or more fatty acid salts may comprise one or more salts of cocoate, stearate, palmitate, laurate, myristate, acyl sarcocinate, or mixtures thereof.

In some embodiments, the solid shaving aid composition may comprise the one or more fatty acid salts and the optional one or more fatty acids in a total amount of between about 17 and about 45 wt.-%, more specifically between about 20 and about 42 wt.-%, and in particular between about 20 wt.-% and about 40 wt.-%, relative to the total weight of the solid shaving aid composition.

In some embodiments, the solid shaving aid composition may comprise sulfur-containing anionic surfactants. The exact composition (i.e. type of compounds and their respective amount) is not particularly limited and may be suitably selected depending on the cleansing and/or foaming properties. The solid shaving aid composition may further comprise, relative to the total weight of the solid shaving aid composition, between about 0.5 wt.-% and about 15 wt.-%, specifically between about 1 wt.-% and about 10 wt.-%, and in particular between about 2 wt.-% and about 9 wt.-% of one or more sulfur-containing anionic surfactants. In some embodiments, the anionic sulfur-containing surfactants may be selected from alkyl sulfates, sulfosuccinates, alkyl benzene sulfonate, acyl methyl taurates, isethionates, monoglyceride sulfates, ether sulfonates and ether sulfates having between about 8 and about 24 carbon atoms, in particular between about 10 and about 20 carbon atoms. Specific examples include $C_{12}$-$C_{20}$-alkyl sulfates and $C_{10}$-$C_{14}$-alkyl poly(oxyethylene) sulfates with a polymerization degree of 1 to about 4.

In the aforementioned context, it should be noted that the present disclosure does not intend to distinguish between tensides, surfactants, and emulsifiers. All these compounds are endowed with a certain degree of surface-active activity and are used interchangeably unless expressly stated otherwise.

The solid shaving aid composition may comprise at least about 35 wt.-% of one or more polyols comprising from about 2 to about 8 carbon atoms.

The exact composition (i.e. type of compounds and their respective amount) is not particularly limited and may be suitably selected depending on the moisturizing and their other properties. Said polyols may have a molecular weight of less than about 250 g/mol. Suitable examples include polyols comprising from about 2 to about 8 carbon atoms and from about 2 and about 7, more specifically from about 2 and about 6, hydroxyl groups. Mixtures of several of such compounds may also be comprised. Suitable polyols may particular be selected from the group consisting of glycerol, sorbitol, ethylene glycol, diethylene glycol, propylene glycol, dipropylene glycol, tripropylene glycol, methylpropane diol glycol, and mixtures thereof.

In some embodiments, the solid shaving aid composition may comprise at least about 38 wt.-% of one or more polyols comprising from about 2 to about 8 carbon atoms, more specifically at least about 40 wt.-%. In some embodiments, the solid shaving aid composition may comprise between about 38 to about 70 wt.-%, and in particular between about 40 wt.-% and about 68 wt.-%.

In some embodiments, the solid shaving aid composition may comprise a relatively large amount of lower-molecular-weight polyols which may be better able to penetrate into the skin and hair and which may have a lower tendency accumulate on the skin, potentially forming a (sticky) film on the surface of the skin. Such lower-molecular-weight polyols may i.a. be characterized by a lower melting point. Accordingly, in some embodiments, the solid shaving aid composition may comprise at least about 15 wt.-%, in particular at least about 20 wt.-%, of polyols having a melting point below about 34° C. In some embodiments, the solid shaving aid composition may comprise at least about 15 wt.-%, in particular at least about 20 wt.-%, of polyols selected from the group consisting of glycerol, ethylene glycol, diethylene glycol, propylene glycol, dipropylene glycol, tripropylene glycol and methylpropane diol glycol. In some embodiments, the solid shaving aid composition may comprise at most about 25 wt.-%, in particular at most about 20 wt.-%, sorbitol.

In some embodiments, the solid shaving aid composition may comprise, as the one or more polyols, relative to the total weight of the solid shaving aid composition:
- about 15 to about 45 wt.-%, in particular about 17 to about 40 wt.-%, glycerol;
- about 5 to about 25 wt.-%, in particular about 6.5 to about 22 wt.-%, sorbitol; and
- about 1.5 to about 9.5 wt.-%, in particular about 2.5 to about 8.5 wt.-%, of a compound selected from propylene glycol, ethylene glycol, dipropylene glycol, tripropylene glycol, methylpropane diol glycol, and mixtures thereof, in particular propylene glycol.

The solid shaving aid composition may comprise about 0.1 to about 3 wt.-% of one or more silicone cross-polymers.

In some embodiments, the one or more silicone cross-polymers may comprise an emulsifying silicone cross-polymer.

In some embodiments, the one or more silicone cross-polymers may comprise a first (di)methicone-based polymer chain which is crosslinked to a second (di)methicone-based polymer chain via at least one hydrophilic oligomer/polymer chain.

In some embodiments, the first and/or second dimethicone-based polymer chain may be selected from dimethicone and optionally substituted linear or branched saturated or unsaturated $C_1$-$C_{20}$ alkyl (di)methicone. In some embodiments, it may be advantageous that the hydrophilic oligomer/polymer chain is a $C_1$-$C_4$-alkyl polyether wherein the $C_1$-$C_4$-alkyl residues are optionally substituted with hydroxyl, hydroxyl-$C_1$-$C_4$-alkyl, $C_1$-$C_4$-alkyl ether groups or hydroxyl-$C_1$-$C_4$-alkylether groups, in particular polyethylene glycol, polypropylene glycol, polyglycerol, and polysorbate. In some embodiments, the one or more silicone cross-polymer may comprise polyglycerine-modified cross-linked polymers, polyether-modified cross-linked polymers, polyether/alkyl co-modified cross-linked polymers, polyglycerine/alkyl co-modified cross-linked polymers, dimethicone/vinyl dimethicone cross-polymers, dimethicone/phenyl vinyl dimethicone cross-polymers, vinyl dimethicone/lauryl dimethicone cross-polymers, dimethicone crosspolymers, $C_{30-45}$-alkyl cetearyl dimethicone cross-polymers, cetearyl dimethicone cross-polymers, in particular dimethicone/vinyl dimethicone cross-polymers, vinyl dimethicone/lauryl dimethicone cross-polymers, vinyl dimethicone/lauryl dimethicone cross-polymers, lauryl dimethicone/polyglycerin cross-polymers, dimethicone/polyglycerin cross-polymers, polyethylene glycol/polypropoylene glycol-dimethicone cross-polymer; and mixtures thereof. In some embodiments, it may be particularly advantageous that the solid shaving aid composition comprises a lauryl dimethicone/polyglycerin cross-polymer.

In some embodiments, the one or more silicone cross-polymers may be present in amounts of about 0.1 to about 1.0 wt.-%, more specifically between about 0.15 to about 0.7 wt.-%, and in particular between about 0.20 wt.-% and about 0.45 wt.-%, relative to the total weight of the solid shaving aid composition.

The solid shaving aid composition may further comprise one or more waxes. The term "wax," in the present disclosure is intended to be used as is well-established in the field of cosmetics and is, in particular, meant to refer to a lipophilic (fatty) compound that is solid at e.g. room temperature (e.g. about 25° C.) with a reversible solid/liquid change of state. The method of measuring the melting point of the wax is not particularly limited and may be measured using a differential scanning calorimeter (DSC), for example the calorimeter sold under the name DSC 3 by the company Mettler Toledo.

In some embodiments, the one or more waxes may have a melting point of at least about 40° C. A higher melting point of the one or waxes may facilitate the film-forming capabilities of the wax and may facilitate retaining the effect on the warm skin of the user or when in contact to warm water. In some embodiments, the wax may have a melting point of at least about 40° C., more specifically at least about 42° C. and in particular at least about 45° C. In some embodiments, the wax may have a melting point range of between about 40° C. and about 120° C., more specifically between about 42° C. and about 100° C., and in particular between about 45° C. and about 80° C.

In some embodiments, the wax may have a solubility in water at about 25° C. of less than about 1000 mg/L, more specifically a solubility of less than 100 mg/L or less than about 10 mg/L, and in particular a solubility of less than about 1 mg/L. In some embodiments, the wax may be substantially insoluble or insoluble in water at about 25° C. The method of determining the solubility of the wax is not particularly limited and may be performed by any suitable means, for instance using a USP Dissolution Apparatus 2 (paddle type). A lower water solubility may also facilitate the aforementioned film-forming capabilities of the wax.

Examples of waxes include the following:

a) Hydrocarbon-Based Wax

In some embodiments, the wax may be a hydrocarbon-based wax. The term "hydrocarbon-based wax" is intended to refer to a wax formed essentially from, or even constituted by, carbon and hydrogen atoms, and possibly oxygen and nitrogen atoms, and not containing any silicon or fluorine atoms. It may contain functional groups such as alcohol, ether, amine and/or amide groups.

In some embodiments, it may be advantageous that the hydrocarbon-based wax is a co-surfactant. The term "co-surfactant" in the present disclosure is intended to be used as is well-established in the field of cosmetics and is, in particular, meant to refer to a second (weaker) surfactant that is used in improve or contribute the performance of a primary surfactant (in this case: the carboxylic acid salt). A weaker co-surfactant has a lower surfactant effectiveness relative to the carboxylic acid salts when tested under otherwise identical conditions. Suitable testing conditions are well-known in the art. An exemplary and convenient measure of surfactant efficiency includes the amount of surfactant needed to reduce the surface tension by 20 mN/m at a surface age of 0.1 s, as disclosed in Miller, Tenside Surfactants Detergents 42(4):204-209; 2005, the disclosure of which is incorporated herein by reference. However, other tests may be used as well. One way in which a co-surfactant may improve or contribute the performance of a primary surfactant is that it facilitates the emulsification provided by the carboxylic acid salts, i.e. it acts as an emulsion stabilizer.

As said before, the present disclosure does not intend to distinguish between tensides, surfactants and emulsifiers. The same applies to the term co-surfactant. All these compounds are endowed with a certain degree of surface-active activity and are used interchangeably unless expressly stated otherwise.

In some embodiments, in particular in cases where the hydrocarbon-based wax is a co-surfactant, it may be particularly advantageous that the hydrocarbon-based wax comprises a linear or branched, saturated or unsaturated, monovalent or multivalent hydrocarbyl alcohol having between about 8 and about 32 carbon atoms, specifically between about 10 and about 28 carbon atoms, and in particular between about 12 about 24 carbon atoms. More specifically, the wax may comprise an (in particular a linear) mono- or divalent alkyl alcohol having between about 8 and about 32 carbon atoms, specifically between about 10 and about 28 carbon atoms, and in particular between about 12 about 24 carbon atoms. In some embodiments, the wax may comprise a fatty alcohol, in particular cetyl alcohol, stearyl alcohol, behenyl alcohol, or mixtures thereof such as cetearyl alcohol. A commercial example includes Lanette O, sold by BASF SE, Germany. A fatty alcohol is the aforementioned sense may in particular be a monovalent linear alkyl alcohol having between about 8 and about 24 carbon atoms.

In some embodiments, the hydrocarbon-based wax may in particular include one or more of paraffinic waxes, polyethylene waxes, (hydrogenated) microcrystalline waxes, ozokerine and Fisher-Tropsch waxes.

b) Ester Wax

In some embodiments the wax may comprise an ester wax, in particular a hydrocarbon-based ester wax. The term "ester wax" in the present disclosure is intended to be used as is well-established in the field of cosmetics and is, in particular, meant to refer to a wax comprising at least one ester group.

In some embodiments, the ester wax is an ester of a $C_{8-40}$-hydrocarbyl carboxylic acid, which may optionally be substituted with one or more heteroatoms such as O, N, S or P, with a $C_2$-$C_8$ polyol having between 2 and 8 hydroxyl groups. In some embodiments, the $C_8$-$C_{40}$-hydrocarbyl carboxylic acid may comprise at least one saturated or unsaturated $C_{10}$-$C_{32}$-moiety, more specifically at least one saturated or unsaturated $C_{12}$-$C_{26}$-moiety, and in particular at least one saturated or unsaturated $C_{14}$-$C_{24}$-moiety. In some embodiments, the $C_2$-$C_8$ polyol has between 2 and 6, between 2 and 4, between 3 and 6, or between 3 and 5 hydroxyl groups. In some embodiments, the ester wax is a monoester, a diester, a triester or a tetraester, and in particular a monoester or diester.

In some embodiments, it may be advantageous that the ester wax still comprises hydroxyl groups, i.e. that the ester is (formally) formed by reaction of less $C_8$-$C_{40}$-hydrocarbyl carboxylic acids than the number of hydroxyl groups in the $C_2$-$C_8$ polyol and/or that the $C_8$-$C_{40}$-hydrocarbyl carboxylic acids are substituted with hydroxyl groups. In some embodiments, it may thus be advantageous that the ester wax comprises one, two, three or four (free) hydroxyl groups. The remaining hydroxyl groups may have the advantage of providing co-surfactant performance to the ester wax.

In some embodiments, the ester wax is an ester of a $C_8$-$C_{40}$-hydrocarbyl alcohol, which may optionally be substituted with one or more heteroatoms such as O, N, S or P, with a $C_2$-$C_8$ carboxylic acid having between 2 and 6 carboxylic acid groups. In some embodiments, the $C_8$-$C_{40}$-hydrocarbyl alcohol may comprise at least one saturated or unsaturated $C_{10}$-$C_{32}$-moiety, more specifically at least one saturated or unsaturated $C_{12}$-$C_{26}$-moiety, and in particular at least one saturated or unsaturated $C_{14}$-$C_{24}$-moiety. In some embodiments, the $C_2$-$C_8$ carboxylic acid has between 2 and 6, between 2 and 4, between 3 and 6, or between 3 and 5 carboxylic acid groups. In some embodiments, the ester wax is a mono ester, a diester, a triester or a tetraester.

In some embodiments, it may be advantageous that the ester wax still comprises hydroxyl groups, i.e. that the ester is (formally) formed by reaction of more $C_8$-$C_{40}$-hydrocarbyl alcohols than the number of carboxylic acid groups in the $C_2$-$C_8$ carboxylic acid and/or that the $C_8$-$C_{40}$-hydrocarbyl alcohols are substituted with hydroxyl groups. In some embodiments, it may thus be advantageous that the ester wax comprises one, two, three or four (free) hydroxyl groups. The remaining hydroxyl groups may have the advantage of providing co-surfactant performance to the ester wax.

In some embodiments, it may be advantageous that the ester wax comprises an ester of a fatty alcohol and/or an ester of a polyol. In some embodiments, the fatty alcohol is as defined above or, alternatively, a $C_8$-$C_{40}$-hydrocarbyl alcohol. In some embodiments, the polyol is a $C_2$-$C_8$ polyol, in particular of glycol or glycerol. In both cases, the carboxy-group may be formed by a fatty acid. A fatty acid is this sense may in particular be a monovalent linear carboxylic acid having between about 8 and about 24 carbon atoms.

Non-limiting examples of ester waxes include:
i) beeswax which is a mixture of ester waxes comprising as its main constituents palmitate, palmitoleate, and oleate esters of long-chain (30-32 carbons) aliphatic alcohols, with the ratio of triacontanyl palmitate $CH_3(CH_2)_{29}O$—$CO$—$(CH_2)_{14}CH_3$ to cerotic acid $CH_3(CH_2)_{24}COOH$, the two principal constituents, being about 6:1.
ii) carnauba wax.
iii) mono- and di-$C_8$-$C_{40}$-hydrocarbyl esters of glycol or glycerol such as glyceryl stearate, glyceryl distearate, glycol stearate and glycol distearate. Such ester waxes are available from SABO S.p.A, Italy.
iv) $C_{20}$-$C_{40}$ alkyl (hydroxystearyloxy)stearates. Such waxes are sold, for example, under the trade names "Kester Wax K 82 P", "Hydroxypolyester K 82 P", "Kester Wax K 80 P", or "Kester Wax K82H" by the company Koster Keunen BV, Netherlands.
v) esters of ethylene glycol and montanic acid (octacosanoic acid). Such waxes are sold, for example, under the trade name "Licowax KPS" by the company Clariant AG, Switzerland.
vi) bis(1,1,1-trimethylolpropane) tetrastearate. Such a wax is sold under the name Hest 2T-4S® by the company Heterene Chemical Co, Inc., USA.
vii) waxes obtained by hydrogenation of castor oil esterified with cetyl alcohol. Such waxes are sold under the trade names Phytowax ricin 16L64® and 22L73® by the company Sophim SA, France.

In some embodiments, it may be particularly advantageous that the ester wax is a carnauba wax.

In some embodiments, the wax may be a mixture of waxes.

In some embodiments, the wax comprises a mixture of at least one hydrocarbon-based wax and at least one ester wax. The hydrocarbon wax may in particular include one or more of polyethylene waxes, (hydrogenated) microcrystalline waxes, ozokerine and Fisher-Tropsch waxes. The ester wax may in particular include a carnauba wax.

In some embodiments, the wax comprises a mixture of at least one hydrocarbon-based wax and at least one ester wax, and the relative amount (by weight) of the hydrocarbon-based wax to the amount (by weight) of the ester wax is between about 10:1 to about 1:10, more specifically between about 5:1 to about 1:5, and in particular between about 3:1 to about 1:3.

In some embodiments, the wax comprises a polar wax. For the purposes of the present disclosure, the term "polar wax" denotes a wax comprising at least one polar group. Polar groups are well known to those skilled in the art: they may i.a. be selected from hydroxyl, ester, carboxylic acid or amide groups. Such polar waxes are to be differentiated from apolar waxes which are hydrocarbon-based and are substantially free or free of the aforementioned polar groups.

Examples of polar waxes include the aforementioned linear or branched, saturated or unsaturated, monovalent or multivalent hydrocarbyl alcohol having between about 8 and about 32 carbon atoms and the aforementioned ester waxes.

In some embodiments, the wax comprises an apolar wax. Examples of such apolar waxes include polyethylene waxes, (hydrogenated) microcrystalline waxes, ozokerine and Fisher-Tropsch waxes.

In some embodiments, the at least one wax may comprise a polar wax and an apolar wax and the weight ratio of the polar wax to the apolar wax may be between about 5:1 to about 1:5, more specifically between about 3:1 to about 1:1.

In some embodiments the solid shaving aid composition may comprise between about 1.0 wt.-% and about 5.0 wt.-%, and in particular between about 2.0 and about 4.0 wt.-%, of the one or more waxes, relative to the total weight of the solid shaving aid composition.

In some embodiments, the solid shaving aid composition may comprise a butter or a mixture of two or more butters.

For the purpose of the present disclosure, the term "butter" is intended to mean a lipophilic fatty compound or composition with a reversible solid/liquid change of state, comprising, in its pure form and at a temperature of about 25° C., a liquid and a solid fraction. In other words, the starting melting point of the butter can be less than about 25° C. The liquid fraction of the butter measured at about 25° C. can represent between about 9 wt.-% and about 97 wt.-% of the compound, more specifically about 15 wt.-% and about 85 wt.-%, and in particular between about 40 wt.-% and about 85 wt.-%.

In some embodiments, the butter(s) may have an end melting point of less than about 60° C.

For the purposes of this disclosure, the melting point of a butter may correspond to the temperature of the most endothermic peak observed on thermal analysis (DSC) as described in Standard ISO 1 1357-3:1999. Said melting point may e.g. be measured using a differential scanning calorimeter (DSC), for example the calorimeter sold under the name DSC Q2000 by the company TA Instruments, USA. As regards the measurement of the melting point and the determination of the end melting point, an exemplary sample preparation and measurement protocols may be as follows:

A sample of 5 mg of the butter, preheated to 80° C. and withdrawn with magnetic stirring using a spatula that is also heated, is placed in a hermetic aluminium capsule, or crucible. Two tests are performed to ensure the reproducibility of the results. The measurements are performed on the abovementioned calorimeter. The oven is flushed with nitrogen. Cooling is provided by an RCS 90 heat exchanger. The sample is then subjected to the following protocol: it is first of all placed at a temperature of 20° C., and then subjected to a first temperature rise passing from 20° C. to 80° C., at a heating rate of 5° C./minute, then is cooled from 80° C. to −80° C. at a cooling rate of 5° C./minute and finally subjected to a second temperature rise passing from −80° C. to 80° C. at a heating rate of 5° C./minute. During the second temperature rise, the variation in the difference in power absorbed by the empty crucible and by the crucible containing the sample of butter is measured as a function of the temperature. The melting point of the butter is the value of the temperature corresponding to the top of the peak of the curve representing the variation in the difference in power absorbed as a function of the temperature.

The end melting point corresponds to the temperature at which 95% of the sample has melted.

The liquid fraction by weight of the butter at 25° C. is equal to the ratio of the heat of fusion consumed at 25° C. to the heat of fusion of the butter.

The heat of fusion of the butter is the heat consumed in order to transition from the solid state to the liquid state. The heat of fusion of the butter is equal to the integral of the entire melting curve obtained using the abovementioned calorimeter, with a temperature rise of 5 or 10° C./minute, according to Standard ISO 1 1357-3:1999. The heat of fusion of the butter is the amount of energy required to make the butter change from the solid state to the liquid state. It is expressed in J/g.

The heat of fusion consumed at 25° C. is the amount of energy absorbed by the sample to change from the solid state to the state that it has at 25° C., consisting of a liquid fraction and a solid fraction.

The liquid fraction of the butter measured at 32° C. may represent from 30% to 100% by weight of the butter, more specifically from 50% to 100%, and in particular from 60% to 100% by weight of the compound. When the liquid fraction of the butter measured at 32° C. is equal to 100%, the temperature of the end of the melting range of the butter is less than or equal to 32° C.

The liquid fraction of the butter measured at 32° C. is equal to the ratio of the heat of fusion consumed at 32° C. to the heat of fusion of the butter. The heat of fusion consumed at 32° C. is calculated in the same way as the heat of fusion consumed at 23° C.

In some embodiments, the butter may have a hardness of less than or equal to about 6 MPa. As regards the measurement of the butter hardness, an exemplary sample preparation and measurement protocols may be as follows:

The butter is placed in a mould 75 mm in diameter, which is filled to about 75% of its height. In order to overcome the thermal history and to control the crystallization, the mould is placed in a Votsch VC0018 programmable oven, where it is first of all placed at a temperature of 80° C. for 60 minutes, then cooled from 80° C. to 0° C. at a cooling rate of 5° C./minute, then left at the stabilized temperature of 0° C. for 60 minutes, and then subjected to a temperature rise passing from 0° C. to 20° C., at a heating rate of 5° C./minute, and then left at the stabilized temperature of 20° C. for 180 minutes.

The compressive force measurement is taken using a TA/TX2i texturometer from Swantech. The spindle used is chosen according to the texture:

cylindrical steel spindle 2 mm in diameter for very rigid starting materials;
cylindrical steel spindle 12 mm in diameter for relatively non-rigid starting materials.

The measurement comprises three steps:

a first step after automatic detection of the surface of the sample, where the spindle moves at a measuring speed of 0.1 mm/second, and penetrates into the composition according to the disclosure or the butter to a penetration depth of 0.3 mm, and the software notes the maximum force value reached;

a second step, known as relaxation, where the spindle remains in this position for one second and where the force is noted after 1 second of relaxation; and finally a third step, known as withdrawal, where the spindle returns to its original position at a speed of 1 mm/second, and the withdrawal energy of the probe (negative force) is noted.

The hardness value measured during the first step corresponds to the maximum compressive force measured in newtons divided by the area of the texturometer cylinder expressed in mm$^2$ in contact with the butter or the composition according to the disclosure. The hardness value obtained is expressed in megapascals or MPa.

Additionally or alternatively, a butter may be characterized in the solid state (at about 25° C.) by an anisotropic crystal organization, which is visible by X-ray observation. Methods for determining the presence of anisotropic crystal organization within butters are not particularly limited and include XRD and in particular X-ray birefringence imaging (XBD).

In some embodiments, the butter(s) is (are) of plant origin, in particular such as those described in Ullmann's Encyclopedia of Industrial Chemistry ("Fats and Fatty Oils", A. Thomas, Published Online: 15 Jun. 2000, DOI: 10.1002/14356007.a10_173, point 13.2.2.2. Shea Butter, Borneo Tallow, and Related Fats (Vegetable Butters)) which are incorporated herein by reference.

In some embodiments, the butter(s) comprise butters selected from the following list: Shea butter, Nilotica shea butter (*Butyrospermum parkii*), galam butter (*Butyrospermum parkii*), Borneo butter or fat or tengkawang tallow (*Shorea stenoptera*), shorea butter, illipe butter, madhuca butter or (Bassia) *Madhuca longifolia* butter, mowrah butter (*Madhuca latifolia*), katiau butter (*Madhuca mottleyana*), phulwara butter (*M. butyracea*), mango butter (*Mangifera indica*), murumuru butter (*Astrocaryum murumuru*), kokum butter (*Garcinia indica*), ucuuba butter (*Virola sebifera*), tucuma butter, painya (kpangnan) butter (*Pentadesma butyracea*), coffee butter (*Coffea arabica*), apricot butter (*Prunus armeniaca*), macadamia butter (*Macadamia ternifolia*), grapeseed butter (*Vitis vinifera*), avocado butter (*Persea gratissima*), olive butter (*Olea europaea*), sweet almond butter (*Prunus amygdalus dulcis*), cocoa butter (*Theobroma cacao*) and sunflower butter.

In some embodiments, the solid shaving aid composition comprises butter(s) selected from shea butter, cocoa butter and/or mango butter.

In some embodiments, the solid shaving aid composition may advantageously comprise cocoa butter and mango butter.

Butters may help in moisturizing dry and irritated skin. Further, butters may provide skin-soothing and regenerative properties. Furthermore, when in contact with warm skin, butters may (partially) melt and provide a film on the skin, which may provide improved glide and maneuverability to the razor.

In some embodiments, the total content of butter(s) may be between 0.5% to 3.5% by weight, more specifically about 0.6 wt.-% to about 3.2 wt.-%, in particular about 0.8% to about 3.0 wt.-%, relative to the total weight of the solid shaving aid composition.

In some embodiments the solid shaving aid composition may further comprise a non-ionic surfactant.

The nonionic surfactants may, for example, be chosen from those compounds that are well known per se (see, for example, "Handbook of Surfactants" by M. R. Porter, published by Blackie & Son (Glasgow and London), 1991, pp. 116-178) which are incorporated herein by reference. The nonionic surfactant may in particular be selected from polyethoxylated, polypropoxylated and polyglycerolated fatty acids, alkylphenols, α-diols and alcohols comprising at least one fatty chain comprising, for example, from about 8 to about 18 carbon atoms, it being possible for the number of ethylene oxide or propylene oxide groups to range, for example, from about 2 to about 200 and for the number of glycerol groups to range, for example, from about 2 to about 100.

In some embodiments, the solid shaving aid comprises polyethoxylated, polypropoxylated and polyglycerolated $C_8$-$C_{30}$ fatty acid with a polymerization degree of 2 to about 200, more specifically a polyethylene glycolester of $C_8$-$C_{30}$ fatty acid, and in particular a polyethylene glycolester of stearic acid with a polymerization degree of 2 to about 200, such as PEG-100 stearate.

The non-ionic surfactants may also be selected from copolymers of ethylene oxide and of propylene oxide, condensates of ethylene oxide and of propylene oxide with $C_8$-$C_{30}$-fatty alcohols; polyethoxylated $C_8$-$C_{30}$-fatty amines, for example, those comprising from about 2 to about 30 mol of ethylene oxide, polyglycerolated $C_8$-$C_{30}$-fatty amides comprising on average from about 1 to about 5 glycerol groups, for example, from about 1.5 to about 4, glycerol groups; polyethoxylated $C_8$-$C_{30}$-fatty amines, for example, comprising from 2 to 30 mol of ethylene oxide; oxyethylenated $C_8$-$C_{30}$-fatty acid esters of sorbitan comprising from 2 to 30 mol of ethylene oxide; $C_8$-$C_{30}$-fatty acid esters of sucrose, $C_8$-$C_{30}$-fatty acid esters of polyethylene glycol, $C_8$-$C_{30}$-alkylpolyglycosides, and N—$C_8$-$C_{30}$-alkylglucamine derivatives.

The non-ionic surfactants may also be selected from alkylpolyglycosides, in particular $C_8$-$C_3$O-alkylpolyglycosides.

In some embodiments the solid shaving aid composition may further comprise a non-ionic surfactant wherein the non-ionic surfactant is not a wax as defined above, in particular not a co-tenside wax.

In some embodiments the solid shaving aid composition may comprise, relative to the total weight of the solid shaving aid composition, less than about 8 wt.-%, more specifically less than about 4 wt.-%, and in particular less than about 2 wt.-%, of the non-ionic surfactant. In some embodiments, the solid shaving aid composition may be substantially free or free of non-ionic surfactants.

Non-ionic surfactants may act as foam enhancers and may reduce skin irritation.

In some embodiments, the solid shaving aid composition may further comprise one or more cationic surfactants. However, in some embodiments, it may be advantageous for compatibility reasons to the anionic surfactants, to keep the amount of such cationic surfactants relatively low. As such, in some embodiments, the solid shaving aid composition may further a total amount of cationic surfactants, relative to the total weight of the solid shaving aid composition, of less than about 5 wt.-%, such as between about 0.1 wt.-% and about 3.0 wt.-%, or between about 0.2 wt.-% and about 1.0 wt.-%.

According to some specific embodiments, the solid shaving aid composition may be substantially free or free of cationic surfactants.

In some embodiments, the solid shaving aid composition further comprises at least one zwitterionic surfactant. The at least one zwitterionic surfactant may comprise a positively charged nitrogen-based group, in particular a quaternary ammonium group, and a negatively charged group, in particular a sulfonate group or carboxylate group. In some embodiments, the at least one zwitterionic surfactant may comprise a betaine, in particular a betaine selected from ($C_8$-$C_{20}$)alkylbetaines, sulfobetaines, ($C_8$-$C_{20}$)alkylamido ($C_1$-$C_6$)alkylbetaines and ($C_8$-$C_{10}$)alkylamido($C_1$-$C_6$)alkylsulfobetaines which may optionally be oxyethylenated.

In some embodiments, the solid shaving aid composition may further comprise one or more oils.

Within the present disclosure, the term "oil" refers to $C_8$-$C_{50}$-substances that are liquid at room temperature (about 25° C.). These oils may be hydrocarbon-based oils of animal, plant, mineral or synthetic origin, silicone oils and/or fluoro oils, and mixtures thereof. The term "hydrocarbon-based oil" refers to an oil mainly containing carbon atoms and hydrogen atoms (e.g. at least about 70 or about 80 atomic wt.-%).

Specific examples of oils that can be used include:
hydrocarbon-based oils of animal origin, such as perhydrosqualene (squalane);
hydrocarbon-based plant oils, such as liquid triglycerides of fatty acids of 4 to 10 carbon atoms, such as heptanoic or octanoic acid triglyceride; coconut oil, sunflower oil, corn oil, soybean oil, marrow oil, grapeseed oil, sesame oil, hazelnut oil, apricot oil, macadamia oil, arara oil, castor oil, avocado oil, caprylic/capric acid triglycerides, and jojoba oil;
linear or branched hydrocarbons of mineral or synthetic origin, such as liquid paraffin and derivatives thereof, petroleum jelly, polydecenes and hydrogenated polyisobutene, such as parleam;
synthetic esters and ethers, in particular, of fatty acids, such as the oils of formula $R_{15}COOR_{16}$ in which $R_{15}$ represents a fatty acid residue containing from about 7 to about 25 carbon atoms and $R_{16}$ represents a hydrocarbon-based chain containing from about 3 to about 25 carbon atoms, such as, for example, purcellin oil, isononyl isononanoate, isopropyl myristate, 2-ethylhexyl palmitate, 2-octyldodecyl stearate, 2-octyldodecyl erucate, isostearyl isostearate; hydroxylated esters such as isostearyl lactate, octyl hydroxystearate, octyldodecyl hydroxystearate, diisostearyl malate, triisocetyl citrate, fatty alkyl heptanoates, octanoates or decanoates; polyol esters such as propylene glycol dioctanoate, neopentyl glycol diheptanoate, diethylene glycol diisononanoate; and pentaerythritol esters such as pentaerythrityl tetraisostearate;

In some embodiments, it may be advantageous that the one or more oils comprises a glycerol esterified with three fatty acids. The fatty acids may be as defined above.

In some embodiments, the solid shaving aid composition may comprise, relative to the total weight of the solid shaving aid composition, between about 0.2 wt.-% to about 6 wt.-%, more specifically between about 0.5 wt.-% and about 4 wt.-%, and in particular between about 1 wt.-% and about 4 wt.-%, of the one or more oils.

Oils may be added to provide a film on the skin, which may improve the glide and maneuverability of the razor. In some embodiments, it may be particularly advantageous that the solid shaving aid composition comprises squalene as the oil.

In some embodiments, the aforementioned one or more oils may comprise one or more humectant oils. A humectant oil may retain water or moisture in the skin. The humectant oils may have a molecular weight of greater than about 500 g/mol, more specifically greater than about 700 g/mol, and in particular greater than about 900 g/mol. In some embodiments the humectant oils may comprise a castor oil derivative, more specifically a castor oil ester, even more specifically a castor oil esterified with 1, 2 or 3 dicarboxylic acid(s) having between about 3 and about 8 carbon atoms. In particular, the humectant oil may comprise castoryl maleate.

In some embodiments, the solid shaving aid composition may comprise, relative to the total weight of the solid shaving aid composition, between about 0.1 wt.-% to about 2 wt.-%, more specifically between about 0.2 wt.-% and about 1 wt.-%, and in particular between about 0.2 wt.-% and about 0.8 wt.-%, of the aforementioned one or more humectant oils having a molecular weight of greater than about 500 g/mol.

In some embodiments, the solid shaving aid composition may comprise, relative to the total weight of the solid shaving aid composition, about 0.1 wt.-% to about 2 wt.-%, more specifically between about 0.2 wt.-% and about 1 wt.-%, and in particular between about 0.2 wt.-% and about 0.8 wt.-%, of the one or more humectant oils having a molecular weight of greater than about 500 g/mol; and, in total, between about 0.2 wt.-% to about 6 wt.-%, more specifically between about 0.5 wt.-% and about 5 wt.-%, and in particular between about 1 wt.-% and about 4 wt.-%, of the one or more oils.

The humectant oil may improve skin hydration. Further, some humectant oils such as castoryl maleate and its derivatives may contribute to providing a film on the skin which may further improve gliding and maneuverability of a razor cartridge.

In some embodiments the solid shaving aid composition may further comprise a number of generally minor optional ingredients which will be discussed below. It should be understood that the below list is not exhaustive and does not exclude the presence of other ingredients not listed below.

In some embodiments the solid shaving aid composition may comprise, relative to the total weight of the solid shaving aid composition, between about 0.5 wt.-% and about 7.0 wt.-%, in particular between about 1.0 wt.-% and about 5.0 wt.-%, of an opacifier or mixture of opacifiers. Suitable opacifiers are not particularly limited and may include inorganic opacifiers such as $TiO_2$, polymeric opacifiers such as styrene/acrylate copolymers, and/or monomeric opacifiers such as the aforementioned wax glycol distearate. For the purposes of calculating compositional amounts, glycol distearate will be considered as a wax and not as an opacifier.

In some embodiments the solid shaving aid composition may comprise, relative to the total weight of the solid shaving aid composition, between about 0.1 wt.-% and about 2.5 wt.-%, in particular between about 0.2 wt.-% and about 1.5 wt.-%, of a fragrance or mixture of fragrances.

In some embodiments the solid shaving aid composition may comprise, relative to the total weight of the solid shaving aid composition, less than 0.01 wt.-%, of an antioxidant or mixture of anti-oxidants. Suitable anti-oxidants are not particularly limited and include catechol derivatives such as hydroxymethoxyphenyl decanone or tocopherol.

In some embodiments the solid shaving aid composition may comprise, relative to the total weight of the solid shaving aid composition, between about 0.01 wt.-% and about 2.0 wt.-%, in particular between about 0.05 wt.-% and about 1.0 wt.-%, of a preservative or mixture of preservatives, in particular an antibacterial agent. Examples include benzyl alcohol, phenoxyethanol and dehydroacetic acid. In some embodiments, the solid shaving aid composition may be substantially free or free of preservative.

In some embodiments, the solid shaving aid composition may comprise water, more specifically about 15 wt.-% to about 50 wt.-%, in particular about 17% to about 45 wt.-%, relative to the total weight of the solid shaving aid composition. The water may function as a solvent or processing aid in preparing the solid shaving aid composition.

In some embodiments, the solid shaving aid composition may comprise a bulking agent. Suitable bulking agents are not particularly limited and include in particular sodium chloride. The bulking agent(s) may be present in amounts of between about 0.5 wt.-% and about 4.2 wt.-%, and in particular between 0.65 wt.-% and about 3.95 wt.-% of one or more bulking agent, relative to the total weight of the solid shaving aid composition.

In some embodiments, the solid shaving aid composition may comprise one or more chelating agents. The one or more chelating agents may comprise a multidentate chelating agent, in particular pentasodium pentetate, tetrasodium etidronate, tetrasodium iminodissucinate, sodium citrate and/or citric acid or mixtures thereof. The solid shaving aid composition may comprise less than about 0.2 wt.-% or less than about 0.3 wt.-% of the one or more chelating agents, relative to the total weight of the solid shaving aid composition.

In some embodiments, the solid shaving aid composition solid shaving aid composition may be substantially free (e.g. less than 0.1 wt.-%, rel. to the total weight of the composition) or free of silicone oil and/or of silicone wax. According to the present disclosure, silicone oils and silicone waxes are not the aforementioned silicone cross-copolymers.

In some embodiments, the solid shaving aid composition may comprise or consist of the following components wherein the components refer to the components as defined above:

a) about 15 wt.-% to about 48 wt.-% of a soap base consisting of one or more fatty acid salts having from about 8 to about 24 carbon atoms and optionally one or more fatty acids having from about 8 to about 24 carbon atoms;

b) about 35 wt.-% to about 75 wt.-% of one or more polyols comprising from about 2 to about 8 carbon atoms, wherein the polyol is in particular selected from the group consisting of glycerol, sorbitol, ethylene glycol, diethylene glycol, propylene glycol, dipropylene glycol, tripropylene glycol, methylpropane diol glycol, and mixtures thereof c) about 0.1 to about 3 wt.-% of one or more silicone cross-polymers;

d) optionally about 1 to about 5% by weight of one or more waxes;

e) optionally about 0.1 to about 3.5% by weight of one or more butters, f) optionally about 0.2 to about 6% by weight of one or more oils, further optionally including about 0.1 to about 2.0% by weight of one or more humectant oils, g) optionally about 15 to about 50% by weight of water, and h) optionally up to about 10% by weight of further ingredients, in particular the further ingredients defined above (cationic surfactants, zwitterionic surfactants, non-ionic surfactants, silicone oils, opacifiers, chelating agents, bulking agents, fragrances, anti-oxidants, preservatives, etc.) but also other non-mentioned ingredients (e.g. colorants, monovalent alcohols, etc.).

In some embodiments, the solid shaving aid composition may comprise two, three or four of components d) to h). In some embodiments, the solid shaving aid composition may comprise all components d) to h). In some embodiments, the solid shaving aid composition may consist of components a) to h).

In some embodiments, for the purposes of calculating compositional amounts, and in case of an overlap, the compound in question will be allotted according to the category of compound first mentioned in the detailed description. For instance, glycol distearate may be classified as both wax and opacifier but for the purposes of calculating compositional amounts, it will be considered as a wax since the compound category of waxes is mentioned before the opacifiers in the detailed description.

In some embodiments the solid shaving aid composition may be configured to last for at least about 8 leg shaves or facial shaves, more specifically at least about 9 leg shaves or facial shaves, and in particular at least about 10 leg shaves or facial shaves. The shaves may also be performed on other body areas, such as underarms, bikini etc.

In some embodiments the solid shaving composition may be shaped into the form of a bar, more specifically a bar configured to be placed onto a razor cartridge, and in particular a bar having a length of between about 30 mm to about 80 mm, a width between about 2 mm and about 10 mm, and a depth of about 0.2 mm to about 4 mm.

The solid shaving aid composition having a composition defined as any combination of the above embodiments, may be used in a multiplicity of facial or leg shaving operations, wherein the facial or leg shaving operations is repeated for at least about 8 times, specifically about 9 times, and in particular at least about 10 times, without replacing the solid shaving aid composition.

In a second aspect, the present disclosure relates to a solid shaving aid composition. The solid shaving aid composition may have a composition as defined for the first aspect of the present disclosure.

In a third aspect, the present disclosure relates to the use of a solid shaving aid composition having a composition defined above in a multiplicity of facial or leg shaving operations, wherein the facial or leg shaving operations is repeated for at least about 8 times, specifically about 9 times, and in particular at least about 10 times, without replacing the solid shaving aid composition.

Specific embodiments according to the third aspect may use any of the solid shaving aid compositions defined for the first aspect of the present disclosure.

EXAMPLE

A representative composition of the present disclosure was prepared by hot mixing the components described in table 1 below.

TABLE 1 shaving aid compositions

| Components | Amount (wt.-%) |
|---|---|
| SOAP BASE (SODIUM STEARATE, SODIUM LAURATE, LAURIC ACID, STEARIC ACID) | 21.5-37.0 |
| C2-C8 POLYOLS (GLYCERIN, SORBITOL, PROPYLENE GLYCOL, DIPROPYLENE GLYCOL) | 40.0-64.7 |

TABLE 1-continued shaving aid compositions

| Components | Amount (wt.-%) |
|---|---|
| SILICONE CROSS-POLYMER (LAURYL DIMETHICONE POLYGLYCERIN-3 CROSSPOLYMER) | 0.2-0.45 |
| WATER | 22.9-41.9 |
| SULFUR-CONTAINING ANIONIC SURFACTANTS (SODIUM LAURETH SULFATE, SODIUM LAURYL SULFATE, SODIUM COCOYL ISETHIONATE) | 2.4-8.7 |
| OILS (SQUALANE, CASTORYL MALEATE) | 0.5-3 |
| WAXES (HYDROGENATED MICROCRYSTALLINE WAX, CARNAUBA WAX, SYNTHETIC WAX, PARAFFIN) | 2-4 |
| BUTTERS (MANGIFERA INDICA (MANGO) SEED BUTTER, THEOBROMA CACAO (COCOA) SEED BUTTER) | 0.6-3.2 |
| OTHER COMPONENTS | 2-10 |
| Total | 100 |

The composition was tested by a standard test panel of female users (N>80 and <100). The female panelists were instructed to daily shave their legs and bikini zone with a razor cartridge equipped with a solid shaving aid composition according to above table 1 over a time period of 10 days. The panelists were further asked to evaluate the durability perception as follows: If you had used this razor outside the framework of this study, would you have considered it too worn out to still be used another time? The answers were aggregated to the percentage of panelists on any given day of use willing to use the razor once more. The panelists were further asked to simultaneously evaluate the close shave in the bikini zone and on the legs as follows: "Evaluate the absence of hair when going against the grain with the fingers." The answers were rated on a scale of 1 to 10 with 1 being poorest and 10 being best.

In a second panel wave, the same panelists were instructed to shave their legs and bikini zone daily with a razor cartridge equipped with a comparative solid shaving aid composition according to WO 2016/162080 A1. The questionnaire to the panelists and the data analysis was the same.

Regarding close shave, the composition according to the present disclosure outperformed the performance of the comparative composition on every day by a statistically significant margin (at least a rating difference of 0.1). Regarding the durability perception, 40% of the users were willing to use the shaving aid composition again after 10 days (i.e. after 10 uses). In contrast, for the above comparative solid shaving aid composition, less than 30% were willing to use it once more after 10 days.

The present disclosure also relates to the following list of embodiments:
1. A razor cartridge comprising:
   a housing having a front edge and a rear edge;
   one or more shaving blades disposed between the front edge and the rear edge; and
   at least one shaving bar disposed in front of the blade(s) and/or rear of the blade(s) which comprises a solid shaving aid composition;
   wherein the solid shaving aid composition comprises, relative to the total weight of the solid shaving aid composition:
   about 15 wt.-% to about 48 wt.-% of a soap base consisting of one or more fatty acid salts having from about 8 to about 24 carbon atoms and optionally one or more fatty acids having from about 8 to about 24 carbon atoms, at least about 35 wt.-% of one or more polyols comprising from about 2 to about 8 carbon atoms, wherein the polyol is in particular selected from the group consisting of glycerol, sorbitol, ethylene glycol, diethylene glycol, propylene glycol, dipropylene glycol, tripropylene glycol, methylpropane diol glycol, and mixtures thereof; and about 0.1 to about 3 wt.-% of one or more silicone cross-polymers.

2. The razor cartridge of clause 1, wherein the one or more fatty acid salts comprises one or more monovalent linear or branched saturated or unsaturated carboxylic acid salts having between about 8 and about 24 carbon atoms, in particular between about 10 and about 20 carbon atoms; and optionally one or more monovalent linear or branched saturated or unsaturated carboxylic acids having between about 8 and about 24 carbon atoms, in particular between about 10 and about 20 carbon atoms.

3. The razor cartridge of clause 1 or clause 2, wherein the one or more fatty acid salts comprises salts of cocoate, stearate, palmitate, laurate, myristate, acyl sarcocinate, or mixtures thereof 4. The razor cartridge of any one of clauses 1 to 3, wherein the solid shaving aid composition comprises the one or more fatty acid salts and the optional one or more fatty acids in a total amount of between about 17 to about 45 wt.-%, more specifically between about 20 to about 42 wt.-%, and in particular between about 20 wt.-% and about 40 wt.-%, relative to the total weight of the solid shaving aid composition.

5. The razor cartridge of any one of clauses 1 to 4, wherein the one or more polyols include polyols comprising from about 2 to about 8 carbon atoms and from about 2 and about 7, more specifically from about 2 and about 6, hydroxyl groups; or a mixture of several such compounds.

6. The razor cartridge of any one of clauses 1 to 5, wherein the one or more polyols comprises a mixture of glycerol and sorbitol or a mixture of glycerol, sorbitol and one or more further polyols selected from the group consisting of propylene glycol, ethylene glycol, diethylene glycol, dipropylene glycol, tripropylene glycol, and methylpropane diol glycol.

7. The razor cartridge of any one of clauses 1 to 6, wherein at least about 15 wt.-%, in particular at least about 20 wt.-%, of the one or more polyols have a melting point below about 34° C.

8. The razor cartridge of any one of clauses 1 to 7, wherein the solid shaving aid composition comprises, as one or more polyols, relative to the total weight of the solid shaving aid composition:
about 15 to about 45 wt.-%, in particular about 17 to about 40 wt.-%, glycerol;
about 5 to about 25 wt.-%, in particular about 6.5 to about 22 wt.-%, sorbitol; and
about 1.5 to about 9.5 wt.-%, in particular about 2.5 to about 8.5 wt.-%, of a compound selected from propylene glycol, ethylene glycol, dipropylene glycol, tripropylene glycol, methylpropane diol glycol, and mixtures thereof, in particular propylene glycol.

9. The razor cartridge of any one of clauses 1 to 8, wherein one or more silicone cross-polymers comprises an emulsifying silicone cross-polymer.

10. The razor cartridge of any one of clauses 1 to 9, wherein one or more silicone cross-polymers comprises a first (di)methicone-based polymer chain which is crosslinked to a second (di)methicone-based polymer chain via at least one hydrophilic oligomer/polymer chain.

11. The razor cartridge of clause 10, wherein the first and/or second dimethicone-based polymer chain is selected from dimethicone and optionally substituted linear or branched saturated or unsaturated $C_1$-$C_{20}$ alkyl (di)methicone.

12. The razor cartridge of clause 10 or clause 11, wherein the hydrophilic oligomer/polymer chain is a $C_1$-$C_4$-alkyl polyether wherein the $C_1$-$C_3$-alkyl residues are optionally substituted with hydroxyl, hydroxyl-$C_1$-$C_4$-alkyl, $C_1$-$C_4$-alkyl ether groups or hydroxyl-$C_1$-$C_4$-alkylether groups, in particular polyethylene glycol, polypropylene glycol, polyglycerol, and polysorbate.

13. The razor cartridge of any one of clauses 1 to 12, wherein the one or more silicone cross-polymer comprises polyglycerine-modified cross-linked polymers, polyether-modified cross-linked polymers, polyether/alkyl co-modified cross-linked polymers, polyglycerine/alkyl co-modified cross-linked polymers, dimethicone/vinyl dimethicone cross-polymers, dimethicone/phenyl vinyl dimethicone cross-polymers, vinyl dimethicone/lauryl dimethicone cross-polymers, dimethicone crosspolymers, $C_{30-45}$-alkyl cetearyl dimethicone cross-polymers, cetearyl dimethicone cross-polymers, in particular dimethicone/vinyl dimethicone cross-polymers, vinyl dimethicone/lauryl dimethicone cross-polymers, vinyl dimethicone/lauryl dimethicone cross-polymers, lauryl dimethicone/polyglycerin cross-polymers, dimethicone/polyglycerin cross-polymers, polyethylene glycol/polypropylene glycol-dimethicone cross-polymer; and mixtures thereof 14. The razor cartridge of any one of clauses 1 to 13, wherein the one or more silicone cross-polymers is present in amounts of about 0.1 to about 1.0 wt.-%, more specifically between about 0.15 to about 0.7 wt.-%, and in particular between about 0.20 wt.-% and about 0.45 wt.-%, relative to the total weight of the solid shaving aid composition.

15. The razor cartridge of any one of clauses 1 to 14, wherein the solid shaving aid composition further comprises, relative to the total weight of the solid shaving aid composition, between about 0.5 wt.-% and about 15 wt.-%, specifically between about 1 wt.-% and about 10 wt.-%, and in particular between about 2 wt.-% and about 9 wt.-% of one or more sulfur-containing anionic surfactants, in particular anionic surfactants selected from alkyl sulfates, sulfosuccinates, alkyl benzene sulfonate, acyl methyl taurates, isethionates, monoglyceride sulfates, ether sulfates and ether sulfonates having between about 8 and about 24 carbon atoms, in particular between about 10 and about 20 carbon atoms.

16. The razor cartridge of any one of clauses 1 to 15, wherein the solid shaving aid composition further comprises water, more specifically about 15 wt.-% to about 50 wt.-%, in particular about 17% to about 45 wt.-%, relative to the total weight of the solid shaving aid composition.

17. The razor cartridge of any one of clauses 1 to 16, wherein the solid shaving aid composition further comprises at least one butter, wherein the total content of butter(s) is between 0.1% to 3.5% by weight, more specifically about 0.6 wt.-% to about 3.2 wt.-%, in particular about 0.8% to about 3.0 wt.-%, relative to the total weight of the solid shaving aid composition.

18. The razor cartridge of clause 17, wherein at least one butter is selected from the group consisting of cocoa butter, mango butter and mixtures thereof 19. The razor cartridge of any one of clauses 1 to 18, wherein the solid shaving aid composition further comprises one or more oils, in particular one or more oils comprising a glycerol esterified with three fatty acids.

20. The razor cartridge of clause 19, wherein the one or more oils comprises one or more humectant oils having a molecular weight of greater than about 500 g/mol, more specifically a castor oil derivative, and in particular castoryl maleate.

21. The razor cartridge of clause 20, wherein the solid shaving aid composition comprises, relative to the total weight of the solid shaving aid composition, between about 0.1 wt.-% to about 2 wt.-%, more specifically between about 0.2 wt.-% and about 1 wt.-%, and in particular between about 0.2 wt.-% and about 0.8 wt.-%, of the humectant oil.

22. The razor cartridge of clause 20 or clause 21, wherein the solid shaving aid composition comprises, relative to the total weight of the solid shaving aid composition, about 0.1 wt.-% to about 2 wt.-%, more specifically between about 0.2 wt.-% and about 1 wt.-%, and in particular between about 0.2 wt.-% and about 0.8 wt.-%, of the one or more humectant oils having a molecular weight of greater than about 500 g/mol; and, in total, between about 0.2 wt.-% to about 6 wt.-%, more specifically between about 0.5 wt.-% and about 4 wt.-%, and in particular between about 1 wt.-% and about 4 wt.-%, of the one or more oils.

23. The razor cartridge of any one of clauses 1 to 22, wherein the solid shaving aid composition further comprises at least one wax, in particular at least one polar wax or at least one apolar wax or a mixture thereof 24. The razor cartridge of clause 23, wherein the polar wax comprises a carnauba wax.

25. The razor cartridge of clause 23, wherein the apolar wax comprises hydrocarbon wax, specifically a polyolefinic wax, a paraffinic wax, an isoparaffinic wax, a naphthenic wax or mixture thereof, and in particular a microcrystalline wax and/or an ozokerite wax.

26. The razor cartridge of any one of clauses 22 to 25, wherein the at least one wax is present amounts of about 1 wt.-% to about 5 wt.-%, in particular in amounts of about 2.0 wt.-% to about 4.0 wt.-%, relative to the total weight of the solid shaving aid composition.

27. The razor cartridge of any one of clauses 23 to 26, wherein the at least one wax comprises the polar wax and the apolar wax and wherein the weight ratio of the polar wax to the apolar wax is between about 5:1 to about 1:5, more specifically between about 3:1 to about 1:1.

28. The razor cartridge of any one of clauses 1 to 27, wherein the solid shaving aid composition further comprises between about 0.5 wt.-% and about 4.2 wt.-%, and in particular between 0.65 wt.-% and about 3.95 wt.-% of one or more bulking agent, relative to the total weight of the solid shaving aid composition.

29. The razor cartridge of clause 28, wherein the bulking agent comprises sodium chloride.

30. The razor cartridge of any one of clauses 1 to 29, wherein the solid shaving aid composition comprises between about 0.5 wt.-% and about 7 wt.-%, and in particular between 1 wt.-% and about 5 wt.-%, of one or more opacifiers, relative to the total weight of the solid shaving aid composition.

31. The razor cartridge of clause 30, wherein the one or more opacifiers comprises an inorganic pigment, in particular titanium dioxide.

32. The razor cartridge of any one of clauses 1 to 31, wherein the solid shaving aid composition comprises one or more chelating agents.

33. The razor cartridge of clause 32, wherein the chelating agent comprises a multidentate chelating agent, in particular pentasodium pentetate, tetrasodium etidronate, tetrasodium iminodissucinate, citric acid, sodium citrate or mixtures thereof 34. The razor cartridge of clause 32 or 33, wherein the solid shaving aid composition comprises less than 0.15 wt.-% of one or more chelating agents, relative to the total weight of the solid shaving aid composition.

35. The razor cartridge of any one of clauses 1 to 34, wherein the solid shaving aid composition further comprises, relative to the total weight of the solid shaving aid composition, between about 0.1 wt.-% and about 2.5 wt.-%, in particular between about 0.3 wt.-% and about 1.5 wt.-%, of a fragrance or mixture of fragrances.

36. The razor cartridge of any one of clauses 1 to 35, wherein the solid shaving aid composition further comprises, relative to the total weight of the solid shaving aid composition, less than 0.01 wt.-%, of an anti-oxidant or mixture of anti-oxidants.

37. The razor cartridge of any one of clauses 1 to 36, wherein the solid shaving aid composition is substantially free or free of silicone oil.

38. The razor cartridge of any one of clauses 1 to 37, wherein the solid shaving aid composition is substantially free or free of silicone wax.

39. The razor cartridge of any one of clauses 1 to 38, wherein the solid shaving aid composition further comprises a non-ionic surfactant.

40. The razor cartridge of clause 39, wherein the non-ionic surfactant is selected from polyethoxylated, polypropoxylated and polyglycerolated fatty acids; alkylphenols; copolymers of ethylene oxide and of propylene oxide; condensates of ethylene oxide and of propylene oxide with fatty alcohols; polyethoxylated fatty amides; polyglycerolated fatty amides; polyethoxylated fatty amines; oxyethylenated fatty acid esters of sorbitan; fatty acid esters of sucrose; fatty acid esters of polyethylene glycol; and alkylpolyglycosides.

41. The razor cartridge of clause 39 or clause 40, wherein the solid shaving aid composition comprises, relative to the total weight of the solid shaving aid composition, less than about 8 wt.-%, more specifically less than about 4 wt.-%, and in particular less than about 2 wt.-%, of the non-ionic surfactant.

42. The razor cartridge of any one of clauses 1 to 41, wherein the solid shaving aid composition is configured to last for at least about 8 leg shaves or facial shaves, more specifically at least about 9 leg shaves or facial shaves, and in particular at least about 10 leg shaves or facial shaves.

43. A solid shaving aid composition having a composition as defined in any one of clauses 1 to 42.

44. The solid shaving composition of clause 43, wherein the solid shaving composition is shaped into the form of a bar, more specifically a bar configured to be placed onto a razor cartridge, and in particular a bar having a length of between about 30 mm to about 80 mm, a width between about 2 mm and about 10 mm, and a depth of about 0.2 mm to about 4 mm.

45. Use of a solid shaving aid composition having a composition as defined in any one of clauses 1 to 43 in a multiplicity of facial or leg shaving operations, wherein the facial or leg shaving operations is repeated for at least about 8 times, specifically about 9 times, and in particular at least about 10 times, without replacing the solid shaving aid composition.

Although the embodiments of the present disclosure have been disclosed for illustrative purposes, those skilled in the art will appreciate that various modifications and alterations are possible, without departing from the spirit of the present disclosure. It is also to be understood that such modifications and alterations are incorporated in the scope of the present disclosure and the accompanying claims.

The invention claimed is:

1. A razor cartridge comprising:
   a housing having a front edge and a rear edge;
   one or more shaving blades disposed between the front edge and the rear edge; and
   at least one shaving bar disposed in front of the blade(s) and/or rear of the blade(s) which comprises a solid shaving aid composition;
   wherein the solid shaving aid composition comprises, relative to the total weight of the solid shaving aid composition:
   about 15 wt.-% to about 48 wt.-% of a soap base consisting of one or more fatty acid salts having from about 8 to about 24 carbon atoms and one or more fatty acids having from about 8 to about 24 carbon atoms,
   at least about 35 wt.-% of one or more polyols comprising from about 2 to about 8 carbon atoms, wherein the polyol is selected from the group consisting of glycerol, sorbitol, ethylene glycol, diethylene glycol, propylene glycol, dipropylene glycol, tripropylene glycol, methylpropane diol glycol, and mixtures thereof, and further wherein the one or more polyols include polyols comprising from about 2 to about 8 carbon atoms and from about 2 to about 7 hydroxyl groups, or a mixture of several such compounds; and
   about 0.1 to about 3 wt.-% of one or more silicone cross-polymers.

2. The razor cartridge of claim 1, wherein the one or more polyols comprises a mixture of glycerol and sorbitol or a mixture of glycerol, sorbitol and one or more further polyols selected from the group consisting of propylene glycol, ethylene glycol, diethylene glycol, dipropylene glycol, tripropylene glycol, and methylpropane diol glycol.

3. The razor cartridge of claim 1, wherein at least about 15 wt.-% of the one or more polyols have a melting point below about 34° C.

4. The razor cartridge of claim 1, wherein the solid shaving aid composition comprises, as one or more polyols, relative to the total weight of the solid shaving aid composition:
   about 15 to about 45 wt.-% glycerol;
   about 5 to about 25 wt.-% sorbitol; and
   about 1.5 to about 9.5 wt.-% of a compound selected from propylene glycol, ethylene glycol, dipropylene glycol, tripropylene glycol, methylpropane diol glycol, and mixtures thereof.

5. The razor cartridge of claim 1, wherein one or more silicone cross-polymers comprises an emulsifying silicone cross-polymer.

6. The razor cartridge of claim 1, wherein one or more silicone cross-polymers comprises a first (di)methicone-based polymer chain which is crosslinked to a second (di)methicone-based polymer chain via at least one hydrophilic oligomer/polymer chain.

7. The razor cartridge of claim 6, wherein the first and/or second (di)methicone-based polymer chain is selected from dimethicone and substituted linear or branched saturated or unsaturated C1-C20 alkyl (di)methicone.

8. The razor cartridge of claim 6, wherein the hydrophilic oligomer/polymer chain is a C1-C4-alkyl polyether wherein the C1-C3-alkyl residues are substituted with hydroxyl, hydroxyl-C1-C4-alkyl, C1-C4-alkyl ether groups or hydroxyl-C1-C4-alkylether groups.

9. The razor cartridge of claim 1, wherein the one or more silicone cross-polymer comprises polyglycerine-modified cross-linked polymers, polyether-modified cross-linked polymers, polyether/alkyl co-modified cross-linked polymers, polyglycerine/alkyl co-modified cross-linked polymers, dimethicone/vinyl dimethicone cross-polymers, dimethicone/phenyl vinyl dimethicone cross-polymers, vinyl dimethicone/lauryl dimethicone cross-polymers, dimethicone crosspolymers, C30-45-alkyl cetearyl dimethicone cross-polymers, cetearyl dimethicone cross-polymers, and mixtures thereof.

10. The razor cartridge of claim 1, wherein the one or more silicone cross-polymers is present in amounts of about 0.1 to about 1.0 wt.-%, relative to the total weight of the solid shaving aid composition.

11. The razor cartridge of claim 1, wherein the solid shaving aid composition further comprises one or more oils.

12. The razor cartridge of claim 11, wherein the one or more oils are present in an amount of between about 0.2 wt.-% to about 6 wt.-%, relative to the total weight of the solid shaving aid composition.

13. The razor cartridge of claim 11, wherein the one or more oils comprises a glycerol esterified with three fatty acids.

14. The razor cartridge of claim 11, wherein the one or more oils comprises one or more humectant oils having a molecular weight of greater than about 500 g/mol.

15. The razor cartridge of claim 14, wherein the one or more humectant oils having a molecular weight of greater than about 500 g/mol are present in an amount of between about 0.1 wt.-% to about 2 wt.-%, relative to the total weight of the solid shaving aid composition.

16. The razor cartridge of claim 14, wherein the one or more humectant oils having a molecular weight of greater than about 500 g/mol comprises a castor oil derivative.

17. The razor cartridge of claim 14, wherein the one or more humectant oils having a molecular weight of greater than about 500 g/mol comprises castoryl maleate.

18. A solid shaving aid composition having a composition as defined in claim 1.

19. The solid shaving composition of claim 18, wherein the solid shaving composition is shaped into the form of a bar.

20. A razor cartridge comprising:
   a housing having a front edge and a rear edge;
   one or more shaving blades disposed between the front edge and the rear edge; and
   at least one shaving bar disposed in front of the blade(s) and/or rear of the blade(s) which comprises a solid shaving aid composition;
   wherein the solid shaving aid composition comprises, relative to the total weight of the solid shaving aid composition:
   about 15 wt.-% to about 48 wt.-% of a soap base consisting of one or more fatty acid salts having from about 8 to about 24 carbon atoms and one or more fatty acids having from about 8 to about 24 carbon atoms,
   at least about 35 wt.-% of one or more polyols comprising from about 2 to about 8 carbon atoms, wherein the polyol is selected from the group consisting of glycerol, sorbitol, ethylene glycol, diethylene glycol, propylene glycol, dipropylene glycol, tripropylene glycol, methylpropane diol glycol, and mixtures thereof;
one or more oils comprising one or more humectant oils having a molecular weight of greater than about 500 g/mol; and
about 0.1 to about 3 wt.-% of one or more silicone cross-polymers.

\* \* \* \* \*